(12) United States Patent
Norris

(10) Patent No.: US 7,403,806 B2
(45) Date of Patent: Jul. 22, 2008

(54) SYSTEM FOR PREFILTERING A PLETHYSMOGRAPHIC SIGNAL

(75) Inventor: Mark A. Norris, Louisville, CO (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/250,201

(22) Filed: Oct. 14, 2005

(65) Prior Publication Data

US 2006/0293575 A1  Dec. 28, 2006

Related U.S. Application Data

(60) Provisional application No. 60/694,767, filed on Jun. 28, 2005.

(51) Int. Cl.
*A61B 5/1455* (2006.01)

(52) U.S. Cl. .................................................. 600/323

(58) Field of Classification Search .............. 600/323, 600/324, 336

See application file for complete search history.

(56) References Cited

U.S. PATENT DOCUMENTS

| | | |
|---|---|---|
| 3,704,706 A | 12/1972 | Herczfeld et al. |
| 4,306,567 A | 12/1981 | Krasner |
| 4,379,460 A | 4/1983 | Judell |
| 4,404,974 A | 9/1983 | Titus |
| 4,510,944 A | 4/1985 | Porges |
| 4,765,340 A | 8/1988 | Sakai et al. |
| 4,777,960 A | 10/1988 | Berger et al. |
| 4,781,201 A | 11/1988 | Wright et al. |
| 4,813,427 A | 3/1989 | Schlaefke et al. |
| 4,860,759 A | 8/1989 | Kahn et al. |
| 4,869,254 A | 9/1989 | Stone et al. |
| 4,884,578 A | 12/1989 | Morgenstern |
| 4,899,760 A | 2/1990 | Jaeb et al. |
| 4,911,167 A | 3/1990 | Corenman et al. |
| 4,930,517 A | 6/1990 | Cohen et al. |
| 4,958,638 A | 9/1990 | Sharpe et al. |
| 4,960,129 A | 10/1990 | DePaola et al. |
| 4,972,842 A | 11/1990 | Korten et al. |
| 5,033,472 A | 7/1991 | Sato et al. |
| 5,078,136 A | 1/1992 | Stone et al. |
| 5,111,817 A | 5/1992 | Clark et al. |
| 5,170,794 A | 12/1992 | Reiche |
| 5,273,036 A | 12/1993 | Kronberg et al. |
| 5,368,224 A | 11/1994 | Richardson et al. |
| 5,385,144 A | 1/1995 | Yamanishi et al. |
| 5,396,893 A | 3/1995 | Oberg et al. |
| 5,423,322 A | 6/1995 | Clark et al. |
| 5,431,159 A | 7/1995 | Baker et al. |
| 5,482,036 A | 1/1996 | Diab et al. |

(Continued)

*Primary Examiner*—Eric F. Winakur
*Assistant Examiner*—Etsub D Berhanu
(74) *Attorney, Agent, or Firm*—Marsh Fischmann & Breyfogle LLP

(57) ABSTRACT

A detector signal in a pulse oximeter is prefiltered, prior to processing so as to determine a physiological parameter value, so as to reduce the effects of artifact in the signal. An exemplary prefilter multiplies signal amplitude values by a quantitude that is inversely proportional to a substantially current amplitude so as to reduce the amplitude of large amplitude sections typically associated with artifact. In one implementation, the quantity is a ratio of an amplitude associated with a clean section of the signal by some exponential factor of a substantially current amplitude. In this manner, artifact affected portions of the signal are deemphasized in subsequent analyses.

19 Claims, 4 Drawing Sheets

U.S. PATENT DOCUMENTS

| | | |
|---|---|---|
| 5,490,505 A | 2/1996 | Diab et al. |
| 5,511,553 A | 4/1996 | Segalowitz |
| 5,553,615 A | 9/1996 | Carim et al. |
| 5,555,882 A | 9/1996 | Richardson et al. |
| 5,575,284 A | 11/1996 | Athan et al. |
| 5,623,933 A | 4/1997 | Amano et al. |
| 5,755,229 A | 5/1998 | Amano et al. |
| 5,766,127 A | 6/1998 | Pologe et al. |
| 5,776,071 A | 7/1998 | Inukai et al. |
| 5,830,137 A | 11/1998 | Scharf |
| 5,853,364 A | 12/1998 | Baker, Jr. et al. |
| 5,862,805 A | 1/1999 | Nitzan |
| 5,865,167 A | 2/1999 | Godik |
| 5,865,756 A | 2/1999 | Peel, III |
| 5,885,213 A | 3/1999 | Richardson et al. |
| 5,902,235 A | 5/1999 | Lewis et al. |
| 5,919,134 A | 7/1999 | Diab |
| 5,931,779 A | 8/1999 | Arakaki et al. |
| 5,934,277 A | 8/1999 | Mortz |
| 5,954,644 A | 9/1999 | Dettling et al. |
| 5,971,930 A | 10/1999 | Elghazzawi |
| 5,980,463 A | 11/1999 | Brockway et al. ........... 600/485 |
| 5,997,482 A | 12/1999 | Vaschillo et al. |
| 6,002,952 A | 12/1999 | Diab et al. |
| 6,011,985 A | 1/2000 | Athan et al. |
| 6,027,455 A | 2/2000 | Inukai et al. ................ 600/490 |
| 6,028,311 A | 2/2000 | Sodickson et al. |
| 6,064,910 A | 5/2000 | Anderson et al. |
| 6,067,462 A | 5/2000 | Diab et al. |
| 6,081,742 A | 6/2000 | Amano et al. ............... 600/513 |
| 6,083,172 A | 7/2000 | Baker, Jr. et al. |
| 6,094,592 A | 7/2000 | Yorkey et al. |
| 6,099,481 A | 8/2000 | Daniels et al. ............. 600/538 |
| 6,129,675 A | 10/2000 | Jay ........................... 600/485 |
| 6,155,992 A | 12/2000 | Henning et al. ............. 600/583 |
| 6,263,222 B1 | 7/2001 | Diab et al. |
| 6,393,311 B1 | 5/2002 | Edgar, Jr. et al. |
| 6,480,733 B1 | 11/2002 | Turcott ....................... 600/516 |
| 6,519,486 B1 | 2/2003 | Edgar, Jr. et al. |
| 6,594,512 B2 * | 7/2003 | Huang ....................... 600/324 |
| 6,650,917 B2 | 11/2003 | Diab et al. |
| 6,810,277 B2 | 10/2004 | Edgar, Jr. et al. |
| 2004/0039273 A1 | 2/2004 | Terry |
| 2006/0200015 A1 * | 9/2006 | Baker, Jr. .................... 600/323 |

* cited by examiner

SYSTEM FOR PREFILTERING A PLETHYSMOGRAPHIC SIGNAL

CROSS REFERENCE TO RELATED APPLICATIONS

This application claims priority from U.S. Provisional Application Ser. No. 60/694,767 entitled "SYSTEM FOR PREFILTERING A PLETHYSMOGRAPHIC SIGNAL", filed on Jun. 28, 2005, the entirety of which is incorporated herein by reference.

FIELD OF THE INVENTION

The present invention relates generally to photoplethysmography and, in particular, to pre-filtering a photoplethysmographic signal so as to reduce the effects of artifact in the signal.

BACKGROUND OF THE INVENTION

Pulse oximeters determine an oxygen saturation level of a patient's blood, or related analyte values, based on transmission/absorption characteristics of light transmitted through or reflected from a patient's tissue. In particular, pulse oximeters generally include a probe for attaching to a patient's appendage such as a finger, earlobe or nasal septum, or another location, particularly in the case of reflective oximeters. The probe is used to transmit pulsed optical signals of at least two wavelengths, typically red and infrared, to the patient's tissue. The transmitted signals are received by a detector that provides an analog electrical output signal representative of the received optical signals. By processing the electrical signal and analyzing signal values for each of the wavelengths at different portions of the patient's pulse cycle, information can be obtained regarding blood oxygen saturation and/or other parameter values such as pulse rate, or blood pressure/blood volume related values.

The algorithms for determining blood oxygen saturation related values are normally implemented in a digital processing unit. Accordingly, one or more analog-to-digital (A/D) converters are generally interposed between the detector and the digital processing unit. Additionally, the detector signal is generally demodulated and demultiplexed by signal processing components. Demodulation involves separating the physiological signal of interest (generally including a more rapidly changing AC portion including a plethysmographic waveform and an optically based "DC" offset due to slowly changing absorption values associated with non-pulsatile tissue absorption) from a carrier waveform associated with the flashing optical sources. Demultiplexing involves separating the different wavelength components associated with the different signal sources. That is, because blood oxygen saturation is calculated based on differential absorption values for different transmitted optical signal wavelengths, the detected signal is generally separated, or demultiplexed, into at least two different wavelength components. Typically, demodulation and demultiplexing have been implemented in analog circuitry operatively disposed between the optical signal detector and the analog-to-digital converter(s), but can be digitally implemented.

A persistent problem in the field of pulse oximetry is eliminating or otherwise accounting for noise and other artifact that can easily obscure or interfere with the pulsatile signals of interest. Some of the sources of this artifact include power line noise, electrical noise from other medical equipment, and artifact associated with patient motion. In this regard, certain filtering techniques have been employed both on the front end (i.e., in the analog circuitry between the optical signal detector and the analog-to-digital converter or converters) and in the back end (i.e., in the digital domain based on the signal from the analog-to-digital converter or converters) of the signal processing components.

Such front end filtering is generally used to filter the modulation signal as opposed to the physiological signal of interest. In this regard, the modulation signal may be approximately in the form of a square wave whereas the physiological signal of interest, which is carried by the modulation signal, may be in the form of a plethysmographic waveform. The front end filtering may include high pass and low pass filtering. For example, a low pass filter may be used to reject certain high frequency electronic noise and a high pass filter may be used to exclude certain low frequency phenomenon. Thus, such front end filtering is generally used to pass a broad frequency range including the modulation frequency or frequencies and is not directed to targeted elimination of interference with respect to the AC portion of the signal.

Back end filtering is sometimes used to filter noise from the physiological signal of interest. This often involves frequency dependent filtering such as bandpass filtering. Unfortunately, some sources of artifact can include frequency components within the physiological range of interest. For example, motion artifact may be observed within the physiological range of interest. With regard to motion, a number of different digital filtering or other compensation algorithms have been proposed or implemented with varying degrees of success. However, in some cases, these algorithms may either fail to satisfactorily address the effects of motion artifact or may filter out useful pulsatile information to an undesirable extent.

Other approaches to addressing artifact involve deemphasizing or excluding parameter calculations deemed to be based on data that is significantly affected by motion or other artifact. For example, presumed high artifact conditions have been identified based on an analysis of a spectrum of the detector signal to identify spectral characteristics indicative of artifact or the absence of spectral characteristics indicative of a well-defined pulsatile signal. In other cases, presumed high artifact conditions have been identified based on a result of calculations deemed unlikely to have a physiological basis, e.g., calculated values corresponding to an unlikely value of arterial oxygen saturation, an abrupt change thereof, or an unlikely variance from a trend in data related to oxygen saturation with respect to a time window under consideration.

Upon identification of such artifact conditions, associated calculated values may be ignored for purposes of determining a result or may be deweighted, for example, by increasing the size of a time window of data used for calculations (thereby presumably reducing the impact the motion affected data on the result) or by applying confidence or weighting factors to each of a series of calculated values used in obtaining a resulting value, so as to achieve a kind of weighted average wherein motion affected data is deemphasized. However, such approaches have had limited success in addressing a variety of motion conditions. Moreover, in some cases, such approaches have required difficult or questionable judgments in distinguishing different motion conditions, have required complicated processing and/or have limited the methodologies available for physiological parameter calculations.

SUMMARY OF THE INVENTION

The present invention relates to prefiltering a detector signal in a medical instrument, such as a pulse oximeter, so as to deemphasize artifact, such as motion artifact, in the signal prior to performing calculations to determine physiological information based on the signal. In this manner, the calculations can proceed, across a range of artifact conditions, without requiring selection between alternative calculations or the results thereof, without associated judgments as to characterization of the motion environment, and without variations or dynamic corrections to the algorithms. Moreover, short intervals of well-defined physiological signals can be effectively utilized to provide meaningful results. Such prefiltering also allows for effective implementation of a variety of calculation processes, including processes executed with respect to time or frequency domain data, over a range of artifact conditions. Such calculations can be implemented substantially free of additional processing for motion correction or compensation.

The present inventor has recognized, in the context of pulse oximetry, that motion is often episodic and has the transient effect of increasing the amplitude of the AC signal, often to the point that the signal of interest is practically obscured. That is, during motion episodes, the AC signal may be viewed as being composed of the superimposition of an artifact signal on the pulsatile signal, resulting in an integrated signal tending to have peaks of greater amplitude (e.g., associated with intervals of constructive interference between the components) than the peaks associated with intervals of substantially clean pulsatile signals having little or no artifact. In connection with certain signal processing techniques, e.g., certain spectral domain analyses, the noisy portions of the signal tend to be emphasized in relation to cleaner portions, which is typically undesirable. This effect is reversed, in accordance with the present invention, by implementing a prefiltering process to deemphasize signal portions believed to be affected by artifact prior to processing to obtain physiological information regarding a patient.

In accordance with one aspect of the present invention, a method and apparatus (collectively "utility") is provided for reducing the amplitude of a portion of a pulse oximeter signal deemed to be affected by artifact. Specifically, the utility involves receiving an electronic signal reflective of one or more optical signals incident on a detector of a pulse oximeter where the electronic signal includes a first temporal portion that is potentially corrupted by artifact. For example, the electronic signal may be an AC signal corresponding to one of the red and infrared channels of a pulse oximeter. The signal is processed such that an amplitude associated with the first temporal portion of the signal is reduced in relation to that of a second temporal portion of the signal. The resulting processed signal can then be used to obtain physiological information regarding the patient, such as a pulse rate or $SpO_2$ value. In one implementation, the noted processing is implemented by a prefilter which operates substantially continuously on the electronic signal such that it is unnecessary to explicitly identify the artifact affected portion of the signal. Alternatively, such a filter may operate intermittently based on identification of specified artifact conditions, such as signal portions exceeding an amplitude threshold or other threshold believed to be related to artifact. The noted utility thus provides a prefiltered signal where the effects of artifact are reduced. This signal can be processed in conventional fashion to obtain the desired physiological information with reduced impact due to artifact.

In accordance with another aspect of the present invention, a utility is provided for identifying an artifact condition based on the amplitude of an oximeter signal. The utility involves receiving an electronic signal reflective of one or more optical signals incident on a detector of a pulse oximeter and identifying, based on an amplitude related analysis of the received signal, an artifact affected portion of the signal. In this regard, an artifact condition may be identified based on an increased amplitude of an AC portion of the signal. For example, the artifact condition may be identified based on an amplitude exceeding a predetermined threshold, a change in the amplitude over a time period exceeding a predetermined threshold or another amplitude-related analysis. Upon identification of the artifact condition, a correction is applied to reduce an effect of the artifact. In this regard, various processes have been developed for reducing the effect of artifact including bandpass filtering around the pulsatile fundamental frequency, motion cancellation, and motion correction factors applied to physiological parameter calculation. Any such correction or combinations thereof may be applied in accordance with the present invention. Alternatively, the noted identification and correction may be implemented by a prefilter, as described above, that operates to reduce the amplitude of the artifact affected portion of the signal.

Any process that has the effect of reducing an amplitude of the artifact affected portion of the signal in relation to a clean portion of the signal may be used in this regard. For example, only the amplitude of the clean portion of the signal may be increased, only the amplitude of the artifact affected portion of the signal may be reduced, or the amplitude of the clean portion may be increased while that of the artifact affected portion is reduced. Alternatively, the amplitude of the artifact affected portion may be increased by a lesser factor than that of the clean portion or the amplitude of the artifact affected portion may be reduced by a greater factor than that of the clean portion. The amplitude of the artifact affected portion may be processed to achieve the effect of multiplying the amplitude by a factor of less than 1.0 (e.g., multiplying by a value less than 1.0 or dividing by a value greater than 1.0). In this regard, an amplitude value of the artifact affected portion may be processed to achieve the effect multiplying the amplitude value by a factor that is inversely proportional to an amplitude related value of the artifact affected signal portion or a multiple or exponential value thereof. As a further alternative, the clean and artifact affected portions of the signal may be processed to achieve the effect of multiplying by a quantity including a ratio of some multiple or exponential factor of a reference amplitude (e.g., associated with a clean signal portion) by some multiple or exponential factor of a substantially current amplitude.

In accordance with a still further aspect of the present invention, a utility is provided for prefiltering an oximeter signal prior to spectral processing. The utility involves receiving a time-based signal reflective of one or more optical signals incident on a detector of a pulse oximeter and performing a correction with respect to a portion of the received time-based signal to reduce an effect of artifact. For example, the signal may be prefiltered as discussed above to reduce the amplitude of an artifact affected portion of the signal in relation to relatively clean signal portions. A transform is then performed on the processed time-based signal to obtain transformed information relative to a second domain. In this regard, the processed, e.g., prefiltered, signal may be subjected to a Fourier transform such as an FFT to yield a frequency domain signal. The transformed information may include the frequency domain signal or parameters thereof such as peak frequency and amplitude values. The transformed information is then processed to obtain physiological information regarding a patient. For example, in the case of frequency domain processing, a fundamental frequency may correspond to pulse rate or a ratio of amplitudes of the fundamental or other peaks of the red and infrared channel signals may be used to obtain an indication of $SpO_2$. It will be appreciated that prefiltering in this regard may assist in identification of the desired spectral peaks relating to pulsatile phenomena, thereby enhancing such conventional spectral domain processing.

BRIEF DESCRIPTION OF THE DRAWINGS

For a more complete understanding of the present invention and further advantages thereof, reference is now made to the following detailed description taken in conjunction with the drawings, in which.

DETAILED DESCRIPTION

Figure 1:
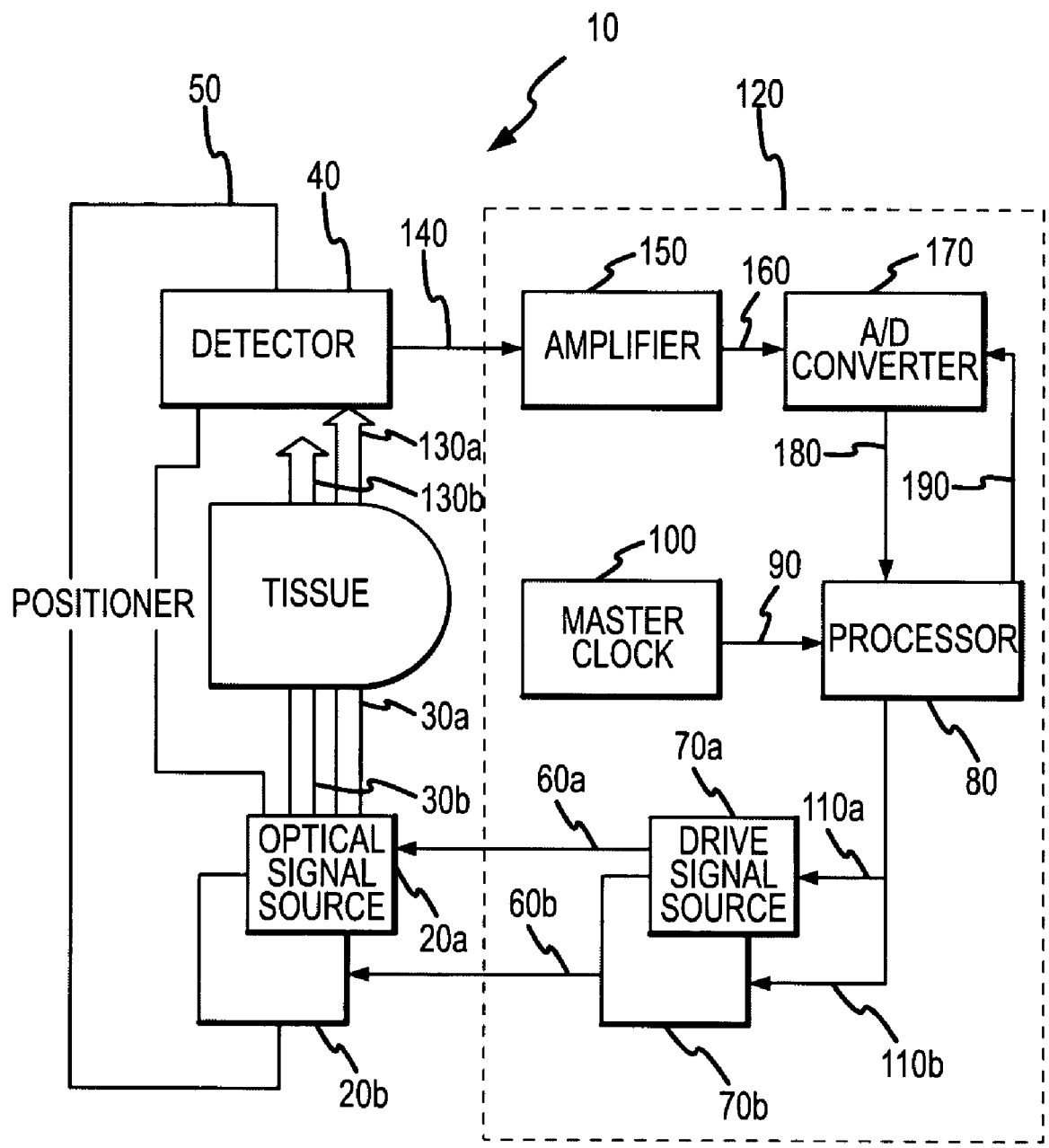
FIG. 1 is a block diagram of a pulse oximeter in accordance with the present invention.

Referring now to FIG. 1, there is shown a block diagram of one embodiment of a pulse oximeter 10 in which a prefilter in accordance with the present invention may be implemented. The pulse oximeter 10 is configured for use in determining the pulse rate of a patient as well as one or more blood analyte levels in the patient, such as an $SpO_2$ level. It should be appreciated that a prefilter in accordance with the present invention may be implemented in pulse oximeters that are configured differently from the pulse oximeter depicted in FIG. 1 as well as in other environments wherein plethysmographic signals are processed in order to obtain desired information relating to patient physiological conditions from the plethysmographic signals.

The illustrated pulse oximeter 10 includes a pair of optical signal sources 20a, 20b for emitting a corresponding pair of light signals 30a, 30b centered at different predetermined center wavelengths $\lambda_1$, $\lambda_2$ through a suitable tissue site of a patient and on to a detector 40 (e.g., a photo-sensitive diode). It will be appreciated that the signals may be reflected from the tissue rather than transmitted through the tissue in accordance with the present invention.

The optical signal sources 20a, 20b and detector 40 may be included in a positioning device 50, or probe structure, to facilitate alignment of the light signals 30a, 30b with the detector 40. For example, the positioning device 50 may be of clip-type or flexible strip configuration adapted for selective attachment to a suitable patient tissue site (e.g., a finger, an ear lobe, a foot, or the nose of the patient). The center wavelengths $\lambda_1$, $\lambda_2$ required depend upon the blood analyte level to be determined. For example, in order to determine an $SpO_2$ level, $\lambda_1$ may be in the red wavelength range and $\lambda_2$ may be in the infrared wavelength range. It should be appreciated that the pulse oximeter 10 may be readily implemented with more optical signal sources (e.g., four) depending, for example, upon the number of different blood analyte levels to be measured.

The optical signal sources 20a, 20b are activated by a corresponding plurality of drive signals 60a, 60b to emit the light signals 30a, 30b. The drive signals 60a, 60b are supplied to the optical signal sources 20a, 20b by a corresponding plurality of drive signal sources 70a, 70b. The drive signal sources 70a, 70b may be connected with a digital processor 80, which is driven with a clock signal 90 from a master clock 100. The digital processor 80 may be programmed to define modulation waveforms, or drive patterns, for each of the optical signal sources 20a, 20b. More particularly, the digital processor 80 may provide separate digital trigger signals 110a, 110b to the drive signal sources 70a-b, which in turn generate the drive signals 60a, 60b. In this regard, the digital trigger signals 110a, 110b may be configured to provide for multiplexing of the drive signals 60a, 60b, and in turn the light signals 30a, 30b, in accordance with a multiplexing scheme (e.g., time division, frequency division, and/or code division multiplexing).

The drive signal sources 70a, 70b, processor 80 and clock 100 may all be housed in a monitor unit 120. While the illustrated embodiment shows the optical signal sources 20a, 20b physically interconnected with the positioning device 50 (e.g., mounted within the positioning device 50 or mounted within a connector end of a cable that is selectively connectable with the positioning device 50), it should be appreciated that the optical signal sources 20a, 20b may also be disposed within the monitor unit 120. In the latter case, the light signals 30a, 30b emitted from the optical signal sources 20a, 20b may be directed from the monitor unit 120 via one or more optical fibers to the positioning device 50 for transmission through the tissue site. Furthermore, the drive signal sources 70a, 70b may comprise a single drive signal generator unit that supplies each of the drive signals 60a, 60b to the optical signal sources 20a, 20b.

Transmitted light signals 130a, 130b (i.e., the portions of light signals 30a, 30b exiting the tissue) are detected by the detector 40. The detector 40 detects the intensities of the transmitted signals 130a, 130b and outputs a current signal 140 wherein the current level is indicative of the intensities of the transmitted signals 130a, 130b. As may be appreciated, the current signal 140 output by the detector 40 comprises a multiplexed signal in the sense that it is a composite signal including information about the intensity of each of the transmitted signals 130a, 130b. Depending upon the nature of the drive signals 60a, 60b, the current signal 140 may, for example, be time division multiplexed, wavelength division multiplexed, and/or code division multiplexed.

The current signal 140 is directed to an amplifier 150, which may be housed in the monitor unit 120 as is shown. As an alternative, the amplifier 150 may instead be included in a probe/cable unit that is selectively connectable with the monitor unit 120. The amplifier 150 converts the current signal 140 to a voltage signal 160 wherein a voltage level is indicative of the intensities of the transmitted signals 130a, 130b. The amplifier 150 may also be configured to filter the current signal 140 from the detector 40 to reduce noise and aliasing. By way of example, the amplifier 150 may include a bandpass filter to attenuate signal components outside of a predetermined frequency range encompassing modulation frequencies of the drive signals 60a, 60b.

Since the current signal 140 output by the detector 40 is a multiplexed signal, the voltage signal 160 is also a multiplexed signal, and thus, the voltage signal 160 is demultiplexed in order to obtain signal portions corresponding with the intensities of the transmitted light signals 130a, 130b. In this regard, the digital processor 80 may be provided with demodulation software for demultiplexing the voltage signal 160. In order for the digital processor 80 to demodulate the voltage signal 160, it is converted from analog to digital. Conversion of the analog voltage signal 160 is accomplished with an analog-to-digital (A/D) converter 170, which may also be included in the monitor unit 120. The A/D converter 170 receives the analog voltage signal 160 from the amplifier 150, samples the voltage signal 160, and converts the samples into a series of digital words 180 (e.g., eight, sixteen or thirty-two bit words), wherein each digital word is representative of the level of the voltage signal 160 (and hence the intensities of the transmitted light signals 130a, 130b) at a particular sample instance. In this regard, the A/D converter 170 preferably provides for sampling of the voltage signal 160 at a rate sufficient to provide for accurate tracking of the shape of the various signal portions comprising the analog voltage signal 160 being converted. For example, the A/D converter 170 may provide for a sampling frequency at least twice the frequency of the highest frequency drive signal 60a, 60b, and more preferably at an even greater sampling rate in order to more accurately represent the analog voltage signal.

The series of digital words 180 is provided by the A/D converter 170 to the processor 80 to be demultiplexed. More particularly, the processor 80 may periodically send an interrupt signal 190 (e.g., once per every eight, sixteen or thirty-two clock cycles) to the A/D converter 170 that causes the A/D converter 170 to transmit one digital word 180 to the processor 80. The demodulation software may then demultiplex the series of digital words 180 in accordance with an appropriate method (e.g., time, frequency and/or code) to obtain digital signal portions indicative of the intensities of each of the transmitted light signals 130a, 130b. In this regard, the demultiplexed digital signal portions comprise time domain plethysmographic signals corresponding to the center wavelengths $\lambda_1$, $\lambda_2$ (e.g., red and infrared) of the optical signal sources 20a, 20b. The red and infrared time domain plethysmographic signals may then be processed by the processor 80 to obtain desired patient physiological condition related information therefrom such as the patient's pulse rate and $SpO_2$ level.

In accordance with the present invention, a pulse oximeter as described above includes a prefilter for prefiltering the detector signal to reduce the effects of artifact in the signal. As noted above, the detector signal generally includes a physiological signal carried by a modulation waveform which generally implements a multiplexing scheme. The physiological signal generally includes a larger, more slowly varying portion commonly referred to as the DC portion, and a smaller, higher frequency portion generally referred to as the AC portion. The AC portion includes the pulsatile signal which is generally of interest for determining pulse rate, $SpO_2$ and the like. However, it has been observed that in periods of high artifact such as certain motion episodes that this AC component can become significantly distorted. This distortion is characterized by a substantial increase in AC amplitude.

Figure 2A:
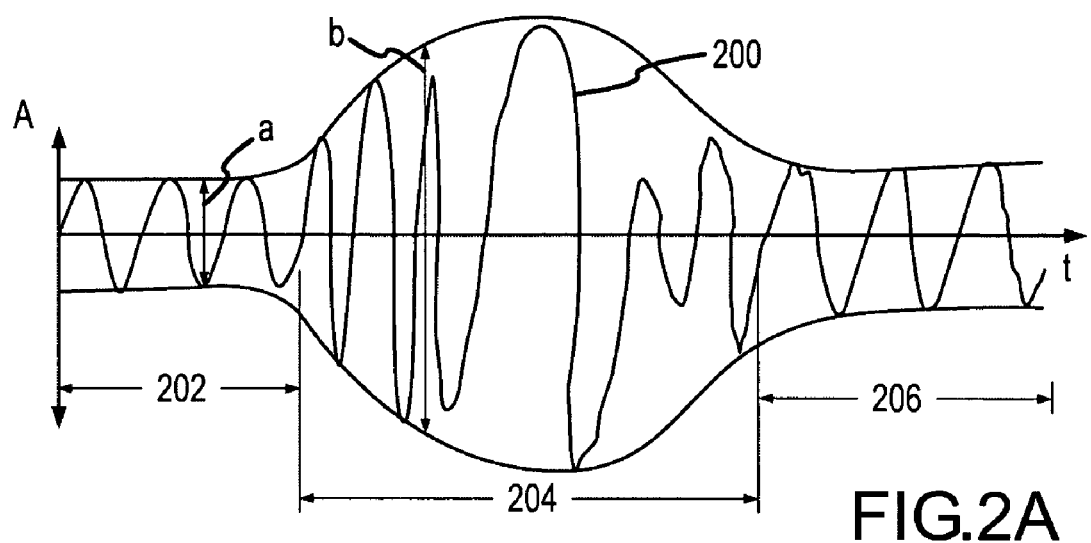
FIGS. 2A-2C illustrate a prefiltering process in accordance with the present invention.

This is generally shown in FIG. 2A. FIG. 2A illustrates an exemplary time interval of an AC signal 200. The illustrated time interval includes an initial relatively clean time period generally indicated at 202 followed by a high artifact interval 204 and concludes with another interval 206 characterized by a relatively clean signal. That is, in intervals 202 and 206, the AC signal 200 is characterized by a relatively well-defined plethysmographic waveform ("pleth"). By contrast, during interval 204, the pleth is substantially distorted by artifact.

Figure 2B:
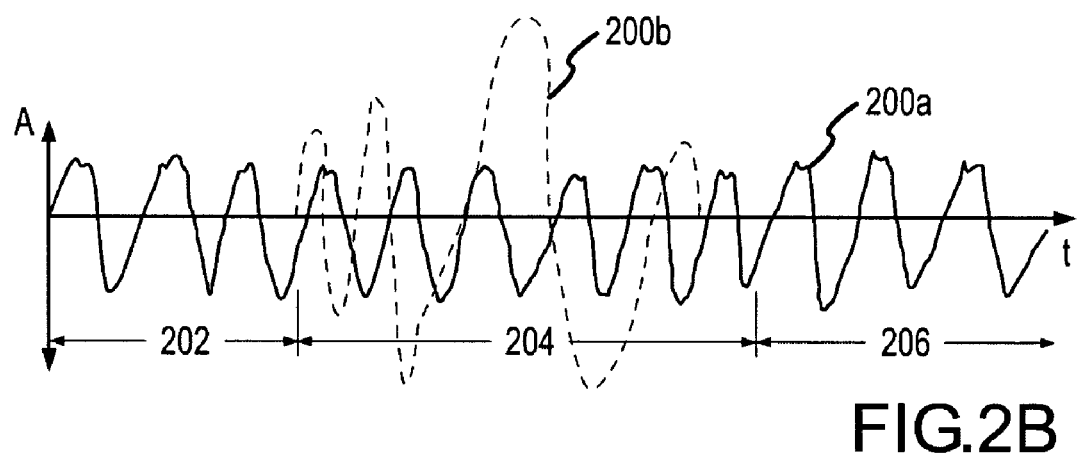

FIG. 2B illustrates a theoretical decomposition of the pulsatile signal 200 into a pulsatile component 200a and an artifact signal 200b during the time interval 204. As shown, it is generally theoretically expected that the pulsatile signal is present during periods of motion. However, the signal is affected by interference by the superimposed artifact signal 200b. One effect of this superimposition of signal components 200a and 200b is that the signal 200a is substantially obscured. Another effect is that the combination of these signals results in an increased amplitude of the composite signal 200 during time interval 204 as shown in FIG. 2A. Unfortunately, when a Fourier transform is performed extending across the integrated time period 202, 204 and 206, the high amplitude portion of the integrated time period, that is, time interval 204, may dominate the resulting spectrum. Consequently, the contributions due to time intervals 202 and 206 are largely overwhelmed.

It will be appreciated that these intervals 202 and 206 of well defined pulsatile signals include useful information which may provide an accurate indication of $SpO_2$, pulse rate and other parameters. Moreover, in many cases, motion is episodic and transient. For example, in connection with monitoring neonates, short intervals of well defined pulsatile signals may be present within an otherwise noisy waveform. It would be desirable to isolate or emphasize these useful signal portions in relation to the surrounding artifact affected portions. However, as previously noted, conventional processing techniques often allow such useful signal portions to be overwhelmed by the artifact affected portions.

In one implementation of the present invention, the AC signal 200 is prefiltered so as to reduce the amplitude of large amplitude signal portions in relation to smaller amplitude signal portions. Because the low amplitude signal portions are believed to generally correspond to clean, well defined pulsatile signals, whereas the larger amplitude portions are believed to correspond to artifact affected signals, such deemphasizing of the large amplitude portions results in a prefiltered signal where the clean signal portions are relatively emphasized. These prefiltered signals can then be processed using conventional techniques to obtain desired physiological information such as $SpO_2$ or pulse rate with reduced impact due to artifact.

The functionality of this prefilter may be understood by reference to FIG. 2A. Specifically, in one implementation, the prefilter utilizes two signal parameters, a and b, to execute a transfer function for generating the prefiltered signal. The parameter a is a measure of the amplitude of pulsatile signal. This value may be obtained in a variety of ways. For example, the value a may be determined by a peak to trough measurement of the AC signal 200 during a time interval deemed to represent a clean waveform, e.g., interval 202 or 206. Alternatively, the value a may be based on the amplitude of a pulsatile spectral peak after performing a transform on the AC signal 200. Many other techniques are available to obtain an indication of the parameter a. In this regard, it should be noted that pulse oximeters generally use a value corresponding to a in determining $SpO_2$. Accordingly, such information may be readily available from calculations performed on preceding time intervals of the AC signal 200. Moreover, as will be understood from the description below, it is not essential that the value of a be determined accurately so long as it provides a reasonable reference value for use in the transfer function as described below.

The second parameter used by the prefilter, b, is a substantially instantaneous measure of the amplitude of the AC signal 200. As shown in FIG. 2A, this value may indicate the instantaneous width of an envelope described by the AC signal 200. Again, this value may be determined in various ways. For example, the value may be determined based on a peak to trough measurement of the time-based AC signal 200. Alternatively, a curve may be fitted to the local extrema of the AC signal 200 to define the upper and lower boundaries of the envelope 208. The instantaneous distance between these boundaries will then define the parameter b. It will be appreciated that many other techniques are possible to determine the parameter b in accordance with the present invention.

The prefilter in the illustrated embodiment then uses the parameters a and b to deemphasize larger amplitude portions of the AC signal 200. The result is to substantially invert the shape of the envelope 208. This can be simply accomplished by implementing the following transfer function.

$$f(n)=a/bx$$

where x is preferably greater than or equal to 1.

Thus, each value of the AC signal 200 is multiplied by the transfer function above to yield a resulting value of the prefiltered signal. In periods of substantially clean pulsatile signal, the value of a will be substantially equal to the value of b. In this case, if the value of a is normalized to be equal to 1.0, the amplitude of the pulsatile signal in the prefiltered waveform will be equal to the amplitude in the unfiltered detector signal. Moreover, in this case, where the amplitude of the AC signal 200 increases relative to the reference value a, the corresponding amplitude of the prefiltered signal will be reduced. The degree of such reduction will depend on the value of x. Currently, it is believed that good results regarding reducing the effects of artifact can be achieved by setting x to be on the order of 2 to 3, but x need not be an integer value.

Figure 2C:
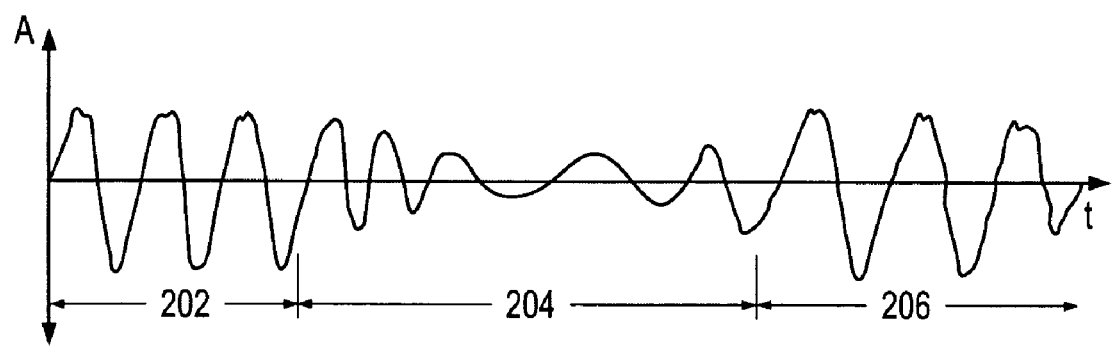

The resulting prefiltered signal is generally illustrated in FIG. 2C. As shown, the relatively clean sections 202 and 206 are substantially unaffected by application of the prefilter. By contrast, the artifact affected section 204, rather than having an increased amplitude as in FIG. 2A, now has a substantially reduced amplitude. As a result, various algorithms applied with respect to the integrated time period 202, 204 and 206 will have a reduced impact due to the artifact. For example, a Fourier transform executed with respect to the integrated time period 202, 204 and 206 will likely reflect larger peaks associated with the pulsatile signal and only smaller peaks corresponding to the artifact signal. This will substantially improve associated calculations to determine values such as pulse rate and $SpO_2$ even without any other modification of the conventional algorithms in this regard.

The prefilter can be implemented in hardware or software. In one implementation, the prefilter is implemented in the processor 80 of FIG. 1. Specifically, the processor receives the AC signal 200 after digitization, and demultiplexing of the detector signal. In addition, the carrier wave and DC portion may be removed from the detector signal. The values of a and b can then be determined as described above to define the prefilter transfer function. The transfer function may be implemented by setting appropriate filter coefficients.

Figure 3:
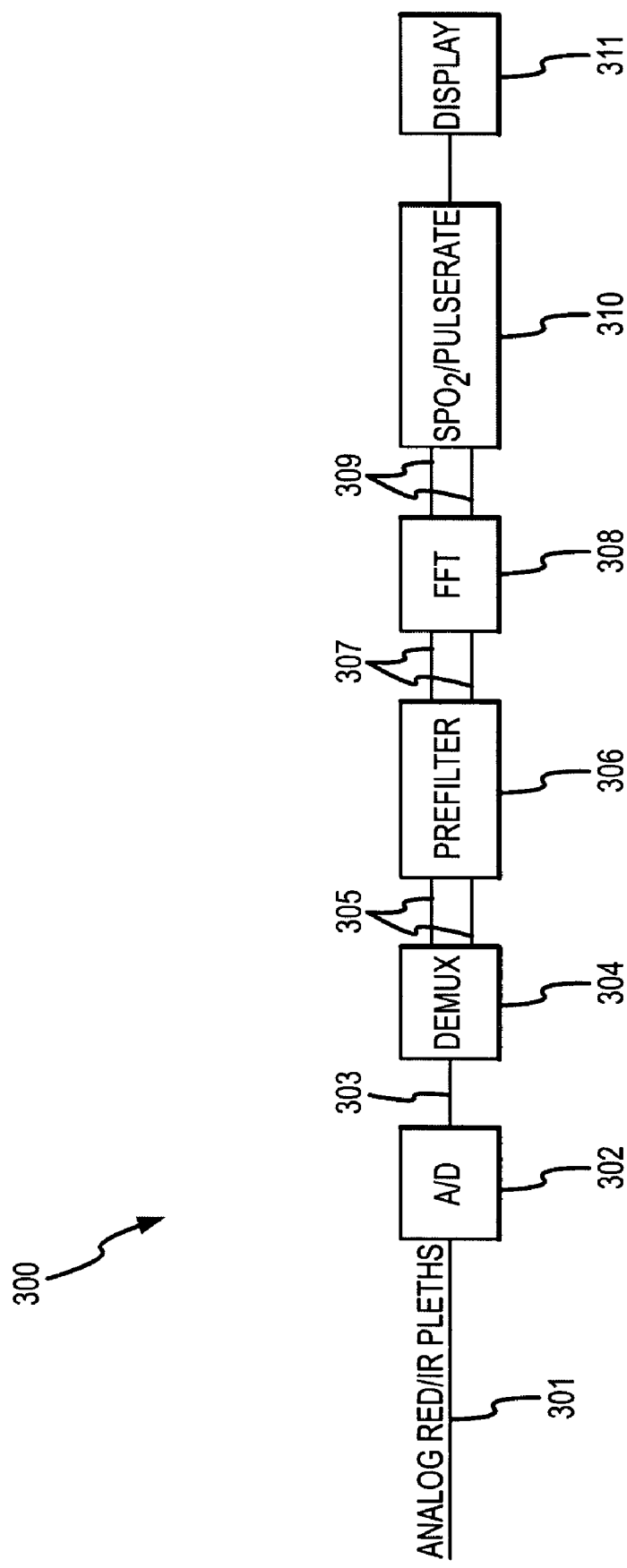
FIG. 3 is a schematic diagram illustrating a system implementing a prefilter in accordance with the present invention.

An associated system 300 including the prefilter is illustrated in FIG. 3. The illustrated system 300 includes an analog to digital converter 302, as generally described above, that receives the analog red and infrared photoplethysmographic signals or pleths, from the detector via certain front end circuitry. The resulting digitized, multiplexed signal 303 is then processed by demultiplexer 304 to provide separate AC signals 305 corresponding to the separate channels of the pulse oximeter. Each of the signals 305 is processed by a prefilter 306 as described above to yield prefiltered signals 307. In the illustrated implementation, these signals 307 are processed by a fast Fourier transform module 308 to yield frequency spectra 309. These spectra 309 are then processed in conventional fashion by $SpO_2$ and pulse rate module 310 to provide pulse rate and oxygen saturation information that can be output to a display 311 of the pulse oximeter. For example, a fundamental peak of one of the spectra may be used to determine pulserate. The fundamental (and/or other) peaks of both spectra may be used to determine $SpO_2$.

Figure 4:
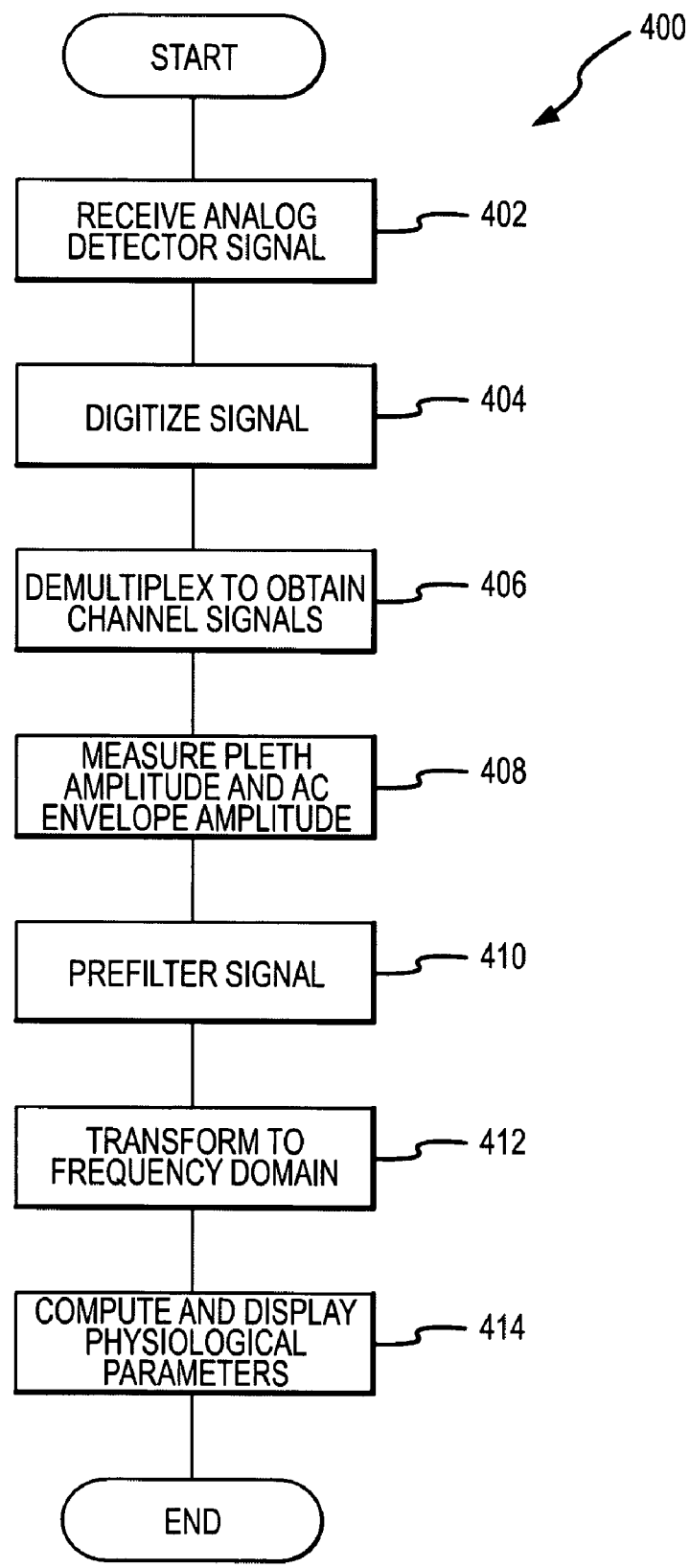
FIG. 4 is a flow chart illustrating a method for processing a detector signal including prefiltering in accordance with the present invention.

A corresponding process 400 can be summarized by reference to the flow chart of FIG. 4. The process 400 is initiated by receiving (402) the analog detector signal. The analog detector signal is then digitized (404) by an A/D converter such as a fast A to D converter as discussed above. The resulting signals are demultiplexed (406) to obtain channel signals corresponding to the red and infrared optical signals of the pulse oximeter. The pleth amplitude and AC envelope amplitude are then measured (408) to provide the parameters used by the prefilter. The signal is then prefiltered (410) so as to deemphasize artifact affected portions of the signal and transformed (412) to obtain frequency domain information, e.g., red and infrared spectra. The frequency domain information is then processed to compute and display (414) the desired physiological parameters such as pulse rate and $SpO_2$.

While various embodiments of the present invention have been described in detail, it is apparent that further modifications and adaptations of the invention will occur to those skilled in the art. However, it is to be expressly understood that such modifications and adaptations are within the spirit and scope of the present invention.

What is claimed is:

1. A method for use in pulse oximetry, comprising the steps of:
   receiving an electronic signal reflective of one or more optical signals incident on a detector of a pulse oximeter, wherein said electronic signal includes a first temporal portion that is potentially corrupted by artifact;
   processing said electronic signal such that an amplitude associated with said first temporal portion of said electronic signal is reduced in relation to less than an amplitude of a second temporal portion of said electronic signal determined to generally correspond to a clean waveform, thereby providing a processed signal; and
   after the processing, using said processed signal to obtain physiological information regarding a patient.

2. A method as set forth in claim 1, wherein said step of processing comprises substantially continuously prefiltering said signal so as to reduce any large amplitude portions thereof.

3. A method as set forth in claim 1, wherein said step of processing comprises monitoring said signal to identify said first temporal portion and selectively reducing said amplitude responsive to said step of identifying.

4. A method as set forth in claim 1, wherein said step of processing comprises processing to achieve the effect of multiplying an amplitude value of said signal corresponding to a time within said first temporal portion by a value less than 1.0.

5. A method as set forth in claim 1, wherein said step of processing comprises processing to achieve the effect of multiplying an amplitude value of said signal corresponding to a time within said first temporal time portion by a variable quantity that is inversely proportional to said amplitude.

6. A method as set forth in claim 5, wherein said variable quantity is inversely proportional to a multiple or exponential factor of said amplitude.

7. A method as set forth in claim 1, wherein said step of processing at least said first temporal portion of said signal uses a first quantity associated with an amplitude of said first portion of said signal and a second quantity associated with said second temporal portion of said signal.

8. A method as set forth in claim 1, wherein said step of using comprises transforming said processed signal into the frequency domain to obtain spectral information and using such spectral information to obtain said physiological information.

9. A method as set forth in claim 8, wherein said physiological information comprises one of a pulserate and an arterial oxygen saturation value for said patient.

10. A method for use in pulse oximetry, comprising the steps of:

receiving a time-based signal reflective of one or more optical signals incident on a detector of a pulse oximeter;

performing a correction with respect to a portion of said received time-based signal to reduce an effect of artifact, thereby providing a processed time-based signal;

performing a transform on said processed time-based signal to obtain transformed information relative to a second domain; and processing the transformed information to obtain physiological information regarding a patient;

wherein said step of performing a correction comprises prefiltering said received time based signal to reduce an amplitude of a portion of said signal determined to be affected by an artifact to a value less than an amplitude of a portion of the signal determined to be clean with reference to the artifact.

11. A method as set forth in claim 10, wherein said step of processing comprises performing a spectral analysis to determine one of a pulse rate and an arterial oxygen saturation value for said patient.

12. An apparatus for use in pulse oximetry, comprising:

a port for receiving an electronic signal reflective of one or more optical signals incident on a detector of a pulse oximeter;

a prefilter for filtering said signal such that an amplitude associated with an artifact affected portion of said signal is reduced in relation to a magnitude less than an amplitude associated with a second portion of said signal that is determined to be associated with a clean waveform, thereby providing a processed signal; and a processor for processing said processed signal after the processing by the prefilter to obtain physiological information regarding a patient.

13. An apparatus as set forth in claim 12, wherein said port comprises input structure associated with the digital signal unit processor.

14. An apparatus as set forth in claim 12, wherein said prefilter is operative for substantially continuously prefiltering said signal source to reduce any large amplitude portions thereof.

15. An apparatus as set forth in claim 12, wherein said prefilter is operative for monitoring said signal to identify said artifact affected portion and selectively reducing said amplitude responsive to said identifying.

16. An apparatus as set forth in claim 12, wherein said processor is operative for calculating one of a pulse rate and an arterial saturation value for said patient.

17. A method for prefiltering a plethysmographic signal, comprising:

receiving a detector signal;

removing a carrier wave and DC portion from the detector signal to generate a pulsatile signal;

providing an amplitude for a clean portion of the pulsatile signal characterized by a relatively well-defined plethysmographic waveform;

processing the pulsatile signal to generate a prefiltered signal by determining an amplitude of a plurality of temporal portions of the pulsatile signal and applying a transfer function to the determined amplitude, wherein the transfer function comprises a ratio of the amplitude of the clean portion to each of the amplitudes of the temporal portions; and after the processing, performing spectral processing of the prefiltered signal to obtain physiological information.

18. The method of claim 17, wherein the transfer function further comprises a multiplication factor applied to the amplitude ratio that is greater than about 1.

19. The method of claim 18, wherein the multiplication factor is less than about 3.

* * * * *

UNITED STATES PATENT AND TRADEMARK OFFICE
CERTIFICATE OF CORRECTION

PATENT NO. : 7,403,806 B2
APPLICATION NO. : 11/250201
DATED : July 22, 2008
INVENTOR(S) : Norris Page 1 of 1

It is certified that error appears in the above-identified patent and that said Letters Patent is hereby corrected as shown below:

Column 12, line 12, delete "phethysmographic" and insert therefor --plethysmographic--.

Signed and Sealed this

Thirtieth Day of September, 2008

JON W. DUDAS
*Director of the United States Patent and Trademark Office*